US005616761A

United States Patent [19]
Geisberger

[11] Patent Number: 5,616,761
[45] Date of Patent: Apr. 1, 1997

[54] PROCESS FOR PREPARAING ALKYL- OR ARYLDICHLOROSILANES

[75] Inventor: Gilbert Geisberger, Altoetting, Germany

[73] Assignee: Wacker-Chemie GmbH, Munich, Germany

[21] Appl. No.: 437,196

[22] Filed: May 8, 1995

[30] Foreign Application Priority Data

Jun. 1, 1994 [DE] Germany .................. 44 19 270.3

[51] Int. Cl.$^6$ .................................................. C07F 7/08
[52] U.S. Cl. ................................................... 556/469
[58] Field of Search ............................................ 556/469

[56] References Cited

U.S. PATENT DOCUMENTS

| | | |
|---|---|---|
| 3,399,222 | 8/1968 | Weyenberg . |
| 3,769,310 | 10/1973 | Viego et al. . |
| 4,410,669 | 10/1983 | Panster et al. . |
| 4,613,491 | 9/1986 | Jung et al. . |
| 4,667,048 | 5/1987 | Inoue et al. ................ 556/469 |
| 4,746,752 | 5/1988 | LePage et al. ............. 556/469 |
| 4,870,200 | 9/1989 | Ottlinger et al. . |
| 5,252,768 | 10/1993 | Geisberger et al. ....... 556/469 |
| 5,416,232 | 5/1995 | Brendler et al. ........... 556/469 |
| 5,434,286 | 7/1995 | Geisberger ................. 556/469 |

FOREIGN PATENT DOCUMENTS

| | | |
|---|---|---|
| 1247325 | 12/1988 | Canada . |
| 0138670 | 4/1985 | European Pat. Off. . |
| 0147834 | 7/1985 | European Pat. Off. . |
| 0206621 | 12/1986 | European Pat. Off. . |
| 0286074 | 10/1988 | European Pat. Off. . |
| 0560363 | 9/1993 | European Pat. Off. . |
| 0600479 | 6/1994 | European Pat. Off. . |
| 1457139 | 10/1966 | France . |
| 4208152 | 9/1993 | Germany . |

OTHER PUBLICATIONS

W. Noll, Chemistry and Technology of Silicones, Academic Press, pp. 87, 88 (1968).
English Derwent Abstract AN 93-289858/37.
K.G. Allum et al., Organometal. Chem. 87, 203–216 (1975).
E.L. Zicky, J. Organometal. Chem. 4, 411–412 (1965).
W. Noll, Chemie und Technologie der Silicone, Verlag Chemie, Weinheim, 2. Auflage pp. 76, 77 (1968).
Chemical Abstracts vol. 107, 1987, p. 135, No. 61394f.

*Primary Examiner*—Paul F. Shaver
*Attorney, Agent, or Firm*—Martin Connaughton

[57] ABSTRACT

The invention relates to a process for preparing alkyl- or aryldichlorosilanes by comproportionation of alkyl- or aryltrichlorosilanes with at least one silane containing Si-bonded methyl groups, hydrogen and/or chlorine atoms in the presence of a catalyst, and also a catalyst.

5 Claims, 1 Drawing Sheet

PROCESS FOR PREPARAING ALKYL- OR ARYLDICHLOROSILANES

FIELD OF INVENTION

The present invention relates to a process for preparing alkyl- or aryldichlorosilanes by comproportionation of alkyl- or aryltrichlorosilanes with at least one silane containing Si-bonded methyl groups, hydrogen and/or chlorine atoms in the presence of a catalyst, and also a catalyst.

BACKGROUND OF INVENTION

U.S. Pat. No. 3,399,222 describes the reaction 2 $RSiCl_3$+ $MeSiH_3 \rightarrow$ 2 $RSiHCl_2$+$MeSiHCl_2$. However, this reaction is carried out in the presence of the homogeneous catalysts $R_4NCl$ or $R_4PCl$.

U.S. Pat. No. 3,769,310 describes a process in which the preparation of alkyl- or aryldichlorosilanes is also mentioned. However, the reactions are homogeneously catalyzed by, for example, $AlCl_3$, $KAlCl_4$.

EP 147834 describes a process in which the preparation of alkyl- or aryldichlorosilanes is also mentioned. The reaction is catalyzed in the presence of crystalline $Al_2O_3$.

DE 4208152 describes a catalyst containing a quaternary ammonium group which is used for catalyzing the transfer of hydrogen to dimethyldichlorosilane.

Disadvantages of the prior art are that use is made of homogeneous catalysts which have to be recovered by means of an additional process step and/or that the processes give the product a low yield.

SUMMARY OF THE INVENTION

It is an object of the present invention to provide an improved process for preparing alkyl- and aryldichlorosilanes and also a catalyst having improved properties in comparison with the prior art.

The invention provides a process for preparing alkyl- or aryldichlorosilanes by comproportionation of alkyl- or aryltrichlorosilanes with at least one silane containing Si-bonded methyl groups, hydrogen and/or chlorine atoms in the presence of a catalyst, wherein the silane used is methylsilane and/or methylchlorosilane and the catalyst used comprises a support insoluble in the reaction medium to which $NR_2R^1$— groups or $X^+NR_3R^1$— groups are bonded, with the $^-X^+NR_3R^1$— groups being preferred, where R is identical or different and is a hydrogen atom or a monovalent hydrocarbon radical having from 1 to 20 carbon atoms per radical or two radicals R together are a divalent hydrocarbon radical having from 4 to 11 carbon atoms which may, if desired, be interrupted by a hetero atom, $R^1$ is a divalent hydrocarbon radical having from 1 to 20 carbon atoms per radical and $X^-$ is a chloride ion, bromide ion or iodide ion.

The process of the invention has the advantage that during the comporportionation an exchange of Si-bonded chlorine atoms and hydrogen atoms occurs, but no exchange of Si-bonded alkyl or aryl groups, therefore, unusable byproducts are not formed. As a result of the heterogeneous catalysis, the reaction products can easily be separated from the catalyst, whereby a continuous process procedure is possible.

The comproportionation of methylsilane and/or methylchlorosilane with an alkyl- or aryltrichlorosilane takes place in the presence of a support insoluble in the reaction medium to which $NR_2R^1$— groups of $^-X^+NR_3R^1$— groups are bonded, where R, $R^1$ and $X^-$are as defined above.

Examples of alkyl and aryl radicals of the alkyl- and aryltrichlorosilanes are alkyl radicals such as the ethyl, n-propyl, iso-propyl, n-butyl, iso-butyl, tert-butyl, n-pentyl, iso-pentyl, neo-pentyl, tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; tetradecyl radicals; hexadecyl radicals and octadecyl radicals such as the n-octadecyl radical; cycloalkyl radicals such as the cyclopentyl, cyclohexyl, cycloheptyl radicals and methylcyclohexyl radicals; aryl radicals such as the phenyl radical; alkaryl radicals such as the o-, m-, p-tolyl radicals; xylyl radicals and ethylphenyl radicals and aralkyl radicals such as the benzyl radical, the α- and β-phenylethyl radical; haloalkyl radicals such as the chloromethyl, 3-chloropropyl and 3-bromopropyl radical; haloaryl radicals such as the o-, m-, p-chlorophenyl and chlorotolyl radical.

Examples radiocals R are alkyl radicals such as the methyl, ethyl, n-propyl, iso-propyl, n-butyl, iso-butyl, tert-butyl, n-pentyl, iso-pentyl, neo-pentyl, tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; tetradecyl radicals; hexadecyl radicals and octadecyl radicals such as the n-octadecyl radical; cycloalkyl radicals such as the cyclopentyl, cyclohexyl, cycloheptyl and methylcyclohexyl radicals; aryl radicals such as the phenyl radical; alkaryl radicals such as the o-, m-, p-tolyl radicals; xylyl radicals and ethylphenyl radicals and aralkyl radicals such as the benzyl radical, the α- and β-phenylethyl radical.

Examples of radicals in which the two radicals R together are a divalent hydrocarbon radical are those of the formulae —$(CH_2)_5$— and —$(CH_2)_4$—.

Examples of radicals in which the two radicals R together are a divalent hydrocarbon radical which is interrupted by a hetero atom are those of the formulae —$(CH_2)_2$—O—$(CH_2)_2$—and —$(CH_2)_2$—O—$(CH_2)_2$—O—$(CH_2)_2$—.

Preferred examples of R are alkyl radicals, with, because of the higher catalytic activity, the n-butyl, n-pentyl, n-hexyl, n-heptyl and n-octyl radical being more preferred.

Examples of radicals $R^1$ are alkylene radicals such as the methylene, ethylene, n-propylene, isopropylene, n-butylene, isobutylene, n-pentylene, iso-pentylene radical; hexylene radicals such as the n-hexylene radical; heptylene radicals such as the n-heptylene radical; octylene radicals such as the n-octylene radical and iso-octylene radicals; nonylene radicals such as the n-nonylene radical; decylene radicals such as the n-decylene radical; dodecylene radicals such as the n-dodecylene radical; tetradecylene radicals; hexadecylene radicals and octadecylene radicals such as the n-octadecylene radical; cycloalkylene radicals such as the cyclopentylene, cyclohexylene and cycloheptylene radicals; arylene radicals such as the phenylene radical; alkarylene radicals such as the tolylene radicals and aralkylene radicals such as the benzylene radical.

Preferred examples of radicals $R^1$ are alkyklene radicals, with the n-propylene, n-butylene, n-pentylene radical being more preferred.

The preferred halide ion X⁻ is the chloride ion.

Preferred supports insoluble in the reaction medium are acid clays such as Tonsil, montmorillonite and other alumiosilicates in the H⁺ form, zeolites, porous glass such as controlled pore glass, porous ceramics such as controlled pore ceramics, porous silicon dioxide such as precipitated or pyrogenic silica, porous aluminum oxide and porous mullite. Particular preference is given to open-pored sintered glass.

Further preferred examples of supports insoluble in the reaction medium are dried hydrolysates of functional silanes or polystyrenes such as polystyrene crosslinked with divinylbenzene.

The NR$_2$R$^1$— or $^{-X+}$NR$_3$R$^1$— groups are bonded to the support using the hydrolyzable groups Y of the compounds of the formula

$$Y_{3-x}R^2{}_xSi\ (CH_2)_nZ \qquad (I)$$

where

Y is the hydrolyzable group,

R$^2$ is a monovalent hydrocarbon radical having from 1 to 12 carbon atoms per radical, n is an integer from 1 to 20, preferably 1 to 12, more preferably 1 to 8, x is 0 or 1, preferably 0, and Z is an NR$_2$— or $^-$X$^+$NR$_3$— group, where R is as defined above, preferably R is identical or different and is a monovalent hydrocarbon radical having from 4 to 8 carbon atoms per radical, X⁻ is as defined above, preferably in an inert solvent such as toluene, chlorobenzene or an alcohol, preferably ethanol, at temperatures in the range of from 0° to 200° C., more preferably in the range from 50° to 100° C.

Examples of hydrolyzable groups Y are alkoxy radicals such as the methoxy, ethoxy, propoxy and butoxy radical, with the ethoxy radical being more preferred, and halogen atoms such as the chlorine atom.

Examples of radicals R$^2$ are alkyl radicals such as the methyl, ethyl, n-propyl, iso-propyl, n-butyl, iso-butyl radical; aryl radicals such as the phenyl radical; and alkaryl radicals such as o-, m-, p-tolyl radicals.

Owing to the ready availability, the preferred radical R$^2$ is the methyl radical and preferred values for n are 2 or 3, i.e., the ethylene or propylene radical.

Examples of preferred compounds of the formula

$$Y_{3-x}R^2{}_xSi\ (CH_2)_nZ \qquad (I)$$

are 3-aminopropyltrimethoxysilane, 3-aminopropyltriethoxysilane, 2-aminoethyltrimethoxysilane, 2-aminoethyltriethoxysilane and 3-aminopropyltrichlorosilane.

Preference is given to using N,N-diethylaminopropyltrimethoxysilane, morpholinopropyltriethoxysilane, trimethoxysilyl-3-propyl-N,N,N-dimethyloctylammonium chloride, trimethoxysilyl-3-propyl-N,N,N-dimethyloctadecylammonium chloride, preferably triethoxysilyl-3-propyl-N,N,N-tripentylammonium chloride, tri- ethoxysilyl-3-propyl-N,N,N-trihexylammonium chloride, triethoxy- silyl-3-propyl-N,N,N-triheptylammonium chloride, triethoxysilyl-3-propyl-N,N,N-trioctylammonium chloride and more preferably triethoxysilyl-3-propyl-N,N,N-tributylammonium chloride.

Preference is given to using 5% to 40% by weight, in particular 25% to 35% by weight, of compounds of formula (I), based on the weight of the untreated support which can be used as powder or preferably as previously finished shaped bodies in the form of round plates, tubes, spheres, rods, honeycomb bodies and preferably Raschig rings.

Preference is given to using a solution having a concentration of from 10% to 60%, preferably from 25% to 35%, of the compound of formula (I) in alcohol, such as methanol, preferably ethanol, or other inert solvents such as toluene, xylene and chlorobenzene, based on the weight of the compound of formula (I).

The NR$_2$R— groups or $^-$X$^+$NR$_3$R$^1$— groups are bonded to the support during the preparation of the hydrolysates of the compound of formula (I), which hydrolysates can be prepared by known methods, in the presence of the support, cf. K. G. Allum et al., Organometal. Chem. 87, 203 (1975).

The catalyst thus obtained in the reaction is preferably dried at a temperature of from 50° to 100° C.

A further possibility is to first partially hydrolyze the compound of formula (I) and only in a second step in the presence of the support to hydrolyze it completely and thus to bind it to the support.

The hydrolysates can also be modified by carrying out the hydrolysis in the presence of further compounds such as water glass, titanium halides or titanium alkoxides, zirconium halides or zirconium alkoxides, aluminum halides or aluminum alkoxides, silicon halides or silicon alkoxides and tin halides or tin alkoxides, with tetraalkoxysilanes such as tetramethoxysilane, tetraethoxysilane, tetrapropoxysilane and tetrabutoxysilane being preferred and tetraethoxysilane being more preferred.

The compounds for modifying the hydrolysates are used in molar amounts of preferably from 1:1 to 5:1, more preferably 3:1, based on the compounds of formula (I).

Examples of the compounds used in the preparation of the hydrolysates are Si (OEt)$_4$ and (EtO)$_3$SiCH$_2$CH$_2$CH$_2$NBu$_3^+$Cl$^-$; Ti (OBu)$_4$ and (MeO)$_3$SiCH$_2$CH$_2$CH$_2$NMe$_2$C$_{18}$H$_{37}^+$Cl$^-$; Na$_2$SiO$_3$ and (MeO)$_3$SiCH$_2$CH$_2$CH$_2$NMe$_2$C$_{10}$H$_{21}^+$Cl$^-$; Al (O-i-Pr)$_3$ and (MeO)$_3$SiCH$_2$CH$_2$CH$_2$NMe$_3^+$Cl$^-$, where Me is a methyl radical, Et is an ethyl radical, i-Pr is an iso-propyl radical and Bu is an n-butyl radical.

The catalysts can be in the form of powder having bonded NR$_2$R$^1$— groups or $^-$X$^+$NR$_3$R$^1$— groups and a mean particle size distribution of preferably from 1 μm to 1 mm, preferably from 0.5 to 1 mm, or have been converted in a manner known before or after the bonding of the NR$_2$R$^1$— groups or $^-$X$^+$NR$_3$R$^1$— groups to the support into shaped bodies such as rings, half-rings, rods, spheres, cubes or saddles. Preferred shaped bodies have the shape of rings, spheres or cubes.

The shaped bodies are shaped from a finely divided catalyst having a mean particle size distribution of from 1 μm to 1 mm, if desired with addition of organic or inorganic binders or with crosslinking hydrolysis. The shaping can be carried out by means of pressing at elevated temperature or by means of sintering under applied pressure, but also by means of an extruder and subsequent comminution of the profiles.

Examples of organic or inorganic binders are epoxy resins, water glass, organic polymers such as polyethylene, polypropylene, polystyrene, polyvinyl chloride, polyacrylate and polyamide.

To increase the porosity of the shaped catalysts, the compositions prior to shaping preferably have added to them a watersoluble substance such as sodium chloride or sodium sulfate which is dissolved out after the shaping step and thus gives a highly active macroporosity.

The support used is more preferably porous silicon dioxide, with a shaped body of open-pored sintered glass (SIRAN®, Schott Glaswerke, Mainz) being especially preferred. This open-pored sintered glass preferably has a surface area of up to 0.4 m²/g, preferably 0.4 m²/g, an adjustable pore volume of up to 70%, a pore diameter of from 1.6 μm to 400 μm and contains silanol groups to which, for example, silanes can be bonded so as to be hydrolytically stable. This shaped body can be used in the form of round plates, tubes, spheres, rods, honeycomb bodies and preferably Raschig rings. The size of the shaped body is preferably 1/10 of the size of the reaction vessel.

The $NR_2R^1$— of $^-X^+NR_3R^1$— groups are preferably bonded to the support surface by impregnating the shaped bodies with compounds of formula (I), preferably in admixture with further compounds, such as silicon alkoxides, in alcohol, such as ethanol, with crosslinking hydrolysis. Use is here made of preferably 5%–40% by weight, in particular 25%–35% by weight, of compounds of formula (I), based on the weight of the untreated support which can be used as powder or preferably as previously finished shaped bodies in the form of round plates, tubes, spheres, rods, honeycomb bodies and preferably Raschig rings. Use is preferably made of a solution of the compound of formula (I) from 10% to 60% strength, preferably from 25% to 35% strength, in alcohol, such as methanol, preferably ethanol, or other inert solvents such as toluene, based on the weight of the compound of formula (I).

The compound of formula (I) is preferably used together with a compound for modifying the hydrolysates, such as silicon alkoxides in molar amounts of from 1:1 to 1:5, preferably 1:3. The subsequent crosslinking hydrolysis is achieved by addition of dilute hydrochloric acid and raising the reaction temperature to a maximum of 100° C., with the solvent distilling off and the catalyst remaining as residue. For complete drying, the catalyst is flushed with air at up to 90° C.

The invention further provides a catalyst comprising a support to which $^-X^+NR_3R^1$— groups are bonded, where R is identical or different and is a monovalent hydrocarbon radical having from 4 to 8 carbon atoms per radical, $R^1$ is a divalent hydrocarbon radical having from 1 to 12, preferably 1 to 8, carbon atoms per radical and $X^-$ is a chloride ion, bromide ion or iodide ion.

The $^-X^+NR_3$— group on the support is preferably bonded to the support via a hydrolyzable group Y of a compound of the formula

$$Y_3Si\,(CH_2)_nZ \qquad (I),$$

where

Y is a hydrolyzable group selected from the group consisting of methoxy, ethoxy, butoxy radicals, n is an integer from 1 to 12, preferably 1 to 8, and Z is an $NR_2$— or preferably $^-X^+NR_3$— group, where R is identical or different and is a monovalent hydrocarbon radical having from 4 to 8 carbon atoms per radical, $X^-$ is as defined above.

The catalyst of the invention preferably has the form of a shaped body of open-pored sintered glass and preferably from 0.05 to 0.2 times the size of the diameter of the reaction vessel.

The catalyst of the invention is prepared as described above.

The methylsilane and/or methylchlorosilane used in the process of the invention is preferably prepared by disproportionation of methyldichlorosilane in the presence of a catalyst. Examples of catalysts are tertiary amines, quaternary ammonium salts such as methyltrioctylammonium chloride, and catalysts comprising a support insoluble in the reaction medium to which tertiary amine groups or quaternary ammonium groups are covalently bonded, as described in U.S. Pat. No. 4,870,200 (Wacker-Chemie GmbH). Particular preference is given to using the catalyst of the invention.

Methylsilane and methylchlorosilane can also be prepared by other methods.

The methylsilane used in the process of the invention can, for example, be prepared from methylhydrogensiloxanes by the process described in E. L. Zicky, J. Organometal. Chem. 4, 411–412 (1965), or by hydrogenation of methylchlorosilanes with metal hydrides as described by W. Noll, Chemie und Technologie der Silicone, Verlag Chemie, Weinheim, 2nd edition, pages 76 and 77, 1968.

The silane starting materials are used in gaseous or liquid form or dissolved in an inert organic solvent such as hexane, toluene, xylene or chlorobenzene.

The solid catalyst is used in finely divided form in a fixed or fluidized bed or preferably as shaped bodies present in a thermostatted tube.

The catalyst is a catalyst comprising a support insoluble in the reaction medium to which $NR_2R^1$— groups or $^-X^+NR_3R^1$— groups are bonded, where R is identical or different, a hydrogen atom or a monovalent hydrocarbon radical having from 1 to 20 carbon atoms per radical or two radicals R together are a divalent hydrocarbon radical having from 4 to 11 carbon atoms, which may be interrupted by a hetero atom, $R^1$ is a divalent hydrocarbon radical having from 1 to 20 carbon atoms per radical and $X^-$ is a chloride ion, bromide ion or iodide ion, with the catalyst of the invention being preferred.

In general the catalyst is arranged in a fixed or fluidized bed, the methylsilane and/or methylchlorosilane is passed together with the alkyl- or aryltrichlorosilane at a pressure of preferably from 0.1 to 15 bar, more preferably from 1 to 5 bar, and a temperature of preferably from 0° to 300° C., more preferably from 50° to 120° C., through a fixed or fluidized bed comprising the catalyst, the reaction mixture obtained is condensed, separated by fractional distillation and the alkyl- or aryldichlorosilane is thus obtained.

Examples of alkyl and aryl radicals of the alkyl- and aryldichlorosilanes are alkyl radicals such as the ethyl, n-propyl, isopropyl, n-butyl, iso-butyl, tert-butyl, n-pentyl, iso-pentyl, neopentyl, tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; tetradecyl radicals; hexadecyl radicals and octadecyl radicals such as the n-octadecyl radical; cycloalkyl radicals such as the cyclopentyl, cyclohexyl, cycloheptyl radical and methylcyclohexyl radicals; aryl radicals such as the phenyl radical; alkaryl radicals such as the o-, m-, p-tolyl radicals; xylyl radicals and ethylphenyl radicals and aralkyl radicals such as the benzyl radical the α- and β-phenylethyl radical; haloalkyl radicals such as the chloromethyl, 3-chloropropyl and 3-bromopropyl radical; haloaryl radicals such as the o-, m-, p-chlorophenyl and chlorotolyl radical.

Preferably use is the methylsilane, methylchlorosilane or a mixture of methylsilane and methylchlorosilane obtained as top product in a rectification column from the disproportionation of methyldichlorosilane, with the disproportionation being carried out with homogeneous or heterogeneous catalysis in the presence of tertiary amines, quaternary ammonium salts and catalysts comprising supports insoluble in the reaction medium to which tertiary amine groups or quaternary ammonium groups are covalently bonded (for example as described in U.S. Pat. No. 4,870,200, Wacker-Chemie GmbH), or preferably the catalyst of the invention.

For the arrangement of the catalyst as shaped bodies in a thermostatted tube, methylsilane and/or methylchlorosilane is passed through together with the alkyl- or aryltrichlorosilane at a pressure of preferably from 0.1 to 20 bar, more preferably from 1 to 3 bar, and at a temperature of preferably from 0° to 250° C., more preferably from 50° to 120° C. The reaction mixture obtained is subsequently separated by fractional distillation.

Preferably used is the methylsilane, methylchlorosilane or a mixture of methylsilane and methylchlorosilane obtained as top product in a rectification column from the disproportionation of methyldichlorosilane, with the disproportionation being carried out with homogeneous or heterogeneous catalysis in the presence of tertiary amines, quaternary ammonium salts and catalysts comprising supports insoluble in the reaction medium to which tertiary amine groups or quaternary ammonium groups are covalently bonded (for example as described in U.S. Pat. No. 4,870,200 Wacker-Chemie GmbH), or more preferably using the catalyst of the invention.

The process of the invention can be carried out batchwise, semi-continuously or continuously. It is preferably carried out continuously. Alkyl- and aryldichlorosilanes are valuable starting compounds for the preparation of functional silanes or siloxanes by hydrosilylation using organic compounds containing aliphatic double or triple bonds.

The methyltrichlorosilane obtained as by-product, mainly in the disproportionation of methyldichlorosilane, can also be economically utilized, for example for the preparation of finely divided silica produced by flame hydrolysis

EXAMPLE 1

Figure 1:
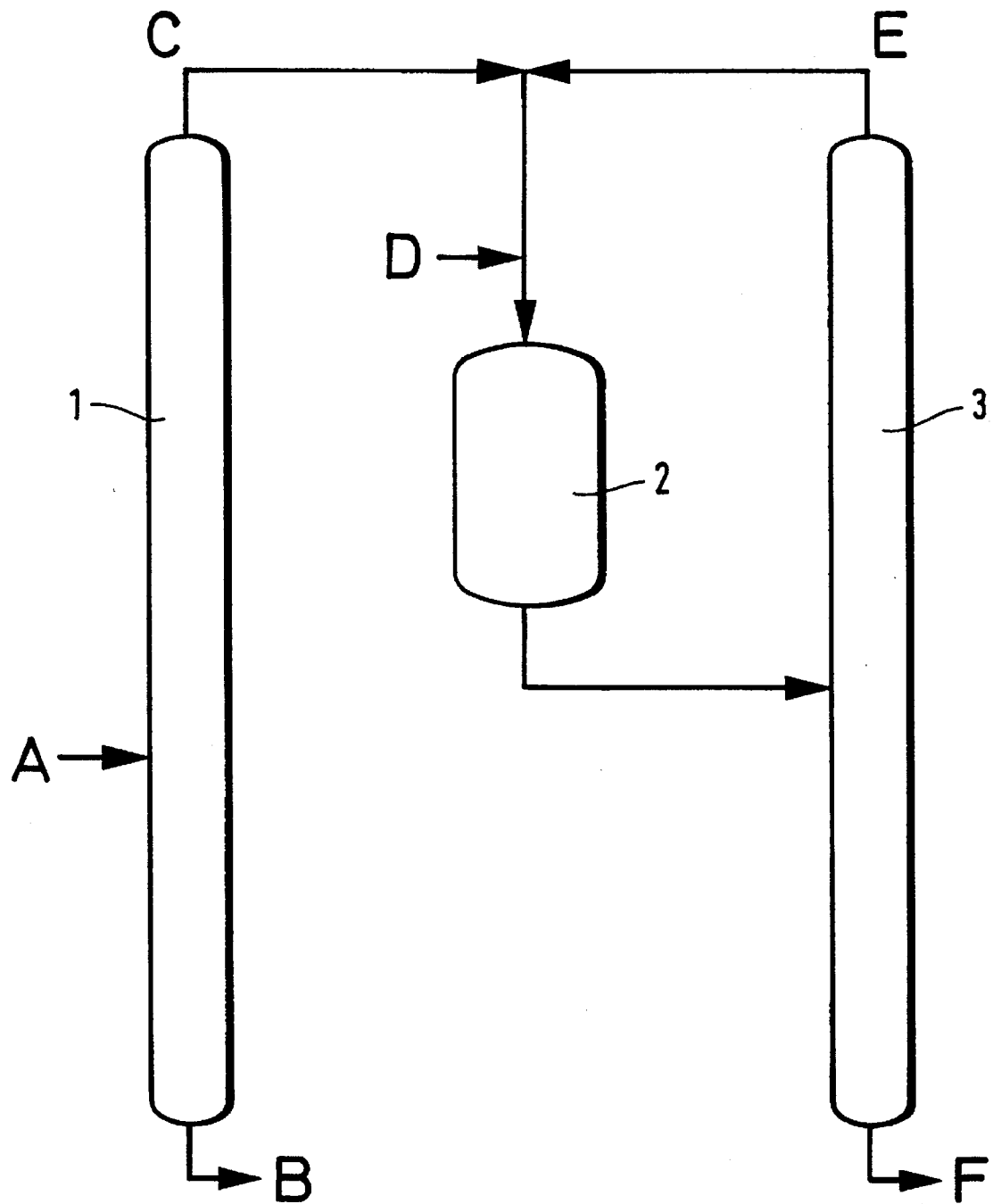
FIG. 1 represents the experimental plant of example 7. Item 1 is a column packed with catalyst prepared in example 1. Item 2 is a thermostatted tube, Item 3 a column similar to item 1 except it is packed with V4A Steel Interpak-10.

Preparation of the catalyst:

1020 g of SIRAN® Raschig rings (9 mm external diameter, Schott Glaswerke, Mainz, FRG) were tumbled in a solution of 306 g of triethoxysilyl-3-propyl-N,N,N-tributylammonium chloride (prepared in an autoclave by maintaining a mixture of 215 g of 3-chloro-propyltriethoxysilane and 185 g of tributylamine in 220 ml of ethanol for 40 hours at 130° C./25 bar and subsequently removing all volatiles in vacuo) and 265 g of tetraethoxysilane in 810 ml of ethanol in a 10 liter flask on a rotary evaporator at room temperature for 30 minutes. Subsequently, 350 ml of 7% strength hydrochloric acid were added, the mixture was maintained at room temperature for 45 minutes and then heated to 93° C. over a period of 3 hours, with the solvent distilling off. The rings were completely dried by flushing with air for 6 hours at 90° C.

EXAMPLES 2 to 6

A thermostatted tube having a diameter of 2.4 cm was charged with the catalyst prepared in accordance with Example 1 to a bed depth of 150 cm. The amounts and compositions of silane passed through were varied (Examples 2 to 6), the products leaving the reaction tube were condensed and analyzed by $^1$H-NMR spectroscopy. The experimental conditions and results are summarized in the table below.

The MeSiH$_3$/MeSiH$_2$Cl mixtures used were prepared by the process described in U.S. Pat. No. 4,870,200, Example 3.

TABLE

| | Examples | | | | |
|---|---|---|---|---|---|
| | 2<br>R = Et | 3<br>R = n-Pr | 4<br>R = i-Bu | 5<br>R = Ph | 6<br>R = Et |
| Starting materials (mol %) | | | | | |
| MeSiH$_3$ | 23.7 | 27.3 | 24.5 | 30.1 | 23.6 |
| MeSiH$_2$Cl | 2.0 | 9.3 | 4.3 | — | 2.0 |
| RSiCl$_3$ | 74.3 | 63.4 | 71.2 | 69.9 | 74.4 |
| Amount of RSiCl$_3$ (g/h) | 200 | 105 | 210 | 200 | 200 |
| Cat. temp (°C.) | 75 | 100 | 100 | 70 | 75 |
| Abs. pressure (bar) | 1 | 1 | 1 | 1 | 1 |
| Product Composition (mol %) | | | | | |
| MeSiH$_3$ | 0.2 | 0.9 | 0.5 | 0.4 | 1.5 |
| MeSiH$_2$Cl | 2.4 | 5.4 | 4.5 | 4.2 | 8.5 |
| MeSiHCl$_2$ | 16.3 | 24.2 | 16.4 | 21.2 | 12.0 |
| MeSiCl$_3$ | 6.8 | 6.0 | 7.5 | 4.3 | 3.6 |
| RSiH$_3$ | 0.5 | 1.5 | 0.4 | 1.3 | 0.2 |
| RSiH$_2$Cl | 4.9 | 8.6 | 8.1 | 10.4 | 3.5 |
| RSiHCl$_2$ | 42.1 | 40.8 | 38.1 | 38.0 | 33.8 |
| RSiCl$_3$ | 26.8 | 12.5 | 24.6 | 20.2 | 36.9 |

EXAMPLE 7

(See FIG. 1)

In an experimental plant 1 made of V4A steel, the essential parts of which are an adjustable metering pump, a vaporizer, a packed column having a total length of 2.5 m and an internal diameter of 50 mm, a column head with condenser, a still pot having a capacity of 5 liter and a device for maintaining constant pressure and discharging the bottoms, 1000 g/h of methyldichlorosilane A, which is continuously vaporized in a vaporizer, and fed at an absolute pressure of 7 bar by means of a metering pump from a reservoir into the lower part of the column.

The methyldichlorosilane, which has been preheated to 95° C., entering the packed column 1 charged with catalyst whose preparation is described in Example 1, disproportionates, with the reaction mixture formed separating at the same time. The higher-boiling methyltrichlorosilane (404 g/h) formed and the unreacted methyldichlorosilane (506 g/h) B collects at the bottom, from where it is discharged into a reservoir. The low boilers go upwards in the column with further reaction. The temperatures in the column are 122° C. at the bottom and 2° C. at the top. The vapor mixture C formed is drawn off at the head of the column and, together with 600 g/h of n-propyltrichlorosilane D, is passed at 2 bar (abs.) through a tube 2 thermostatted to 100° C., having a diameter of 5 cm and a length of 150 cm and charged with catalyst prepared in accordance with Example 1; the reaction product is completely condensed by means of a condenser and introduced at atmospheric pressure into the middle of a rectification column 3 which has the same dimensions as the first column but is charged with V4A steel Interpak-10 packing. The low boilers methylsilane, n-propylsilane and methylchlorosilane E are taken off at the head of the column and are fed to the reactor 2. From the bottom of the column 3, 680 g/h of a silane mixture F of the following composition are continuously taken:

45.6% by weight propyldichlorosilane
19.8% by weight propyltrichlorosilane
7.2% by weight propylchlorosilane
18.6% by weight methyldichlorosilane
8.8% by weight methyltrichlorosilane The silanes are separated by working up the mixture by distillation.

What is claimed is:

1. A process for preparing alkyl- or aryldichlorosilanes by comproportionation of alkyl- or aryltrichlorosilanes with at least one silane containing Si-bonded methyl groups, hydrogen, chlorine atoms or mixtures thereof, in the presence of a catalyst, wherein the silane is methylsilane, methylchlorosilane or mixtures of methylsilane and methylchlorosilane and the catalyst comprises a support insoluble in the reaction medium to which $NR_2R^1$— groups or $^-X^+NR_3R^1$— groups are bonded, where R is identical or different and is a hydrogen atom or a monovalent hydrocarbon radical having from 1 to 20 carbon atoms per radical or two radicals R together are a divalent hydrocarbon radical having from 4 to 11 carbon atoms which may, optionally, be interrupted by a hetero atom, $R^1$ is a divalent hydrocarbon radical having from 1 to 20 carbon atoms per radical and $X^-$ is a chloride ion, bromide ion or iodide ion.

2. The process as claimed in claim 1, wherein the catalyst used is a catalyst comprising a heterogeneous support to which $^-X^+NR_3R^1$— groups are bonded, where R is identical or different and is a monovalent hydrocarbon radical having from 4 to 8 carbon atoms per radical, $R^1$ is a divalent hydrocarbon radical having from 1 to 8 carbon atoms per radical and $X^-$ is a chloride ion, bromide ion or iodide ion.

3. The process as claimed in claim 1, wherein the catalyst comprises a support to which the hydrolyzable group Y of a compound of the formula $$Y_3Si\,(CH_2)_nZ \qquad\qquad (I),$$

where

Y is a hydrolyzable group selected from the group consisting of methoxy, ethoxy, butoxy radicals, n is an integer from 1 to 12, and Z is a $^-X^+NR_3$— group, where R is identical or different and is a monovalent hydrocarbon radical having from 4 to 8 carbon atoms per radical, and $X^-$ is a chloride ion, bromide ion or iodide ion, is bonded.

4. The process as claimed in claim 1, wherein the support is a shaped body and is from 0.05 to 0.2 times the size of the diameter of a vessel in which the process is carried out.

5. The process as claimed in claim 1, wherein the silane are disproportionation products of methyldichlorosilane, which products are obtained by disproportionation of methyldichlorosilane in the presence of a catalyst comprising a support to which $^-X^+NR_3R^1$ groups are bonded, where R is identical or difference and is a monovalent hydrocarbon radical having from 4 to 8 carbon atoms per radical, $R^1$ is a divalent hydrocarbon radical having from 1 to 12 carbon atoms per radical, and $^-X$ is a chloride ion, bromide ion, or iodide ion.

* * * * *